United States Patent [19]

Ali et al.

[11] 4,221,706
[45] Sep. 9, 1980

[54] CHROMOGENIC SUBSTRATES

[75] Inventors: Akhtar Ali, Vernon Hills; Jacob J. Plattner, Libertyville, both of Ill.

[73] Assignee: Abbott Laboratories, North Chicago, Ill.

[21] Appl. No.: 48,409

[22] Filed: Jun. 14, 1979

[51] Int. Cl.³ .................. C07C 103/52; C12Q 1/56; C12Q 1/38; C12Q 1/36
[52] U.S. Cl. .................. 260/112.5 R; 435/23; 435/13; 435/24
[58] Field of Search .................. 260/112.5 R; 438/13; 435/23, 24

[56] References Cited

U.S. PATENT DOCUMENTS

| | | | |
|---|---|---|---|
| 3,748,044 | 7/1973 | Liston | 260/112.5 R |
| 3,884,896 | 5/1975 | Blomback et al. | 260/112.5 R |
| 4,070,245 | 1/1978 | Svendsen | 260/112.5 R |

Primary Examiner—Delbert R. Phillips
Attorney, Agent, or Firm—John J. McDonnell

[57] ABSTRACT

The present invention comprises compounds of the formula

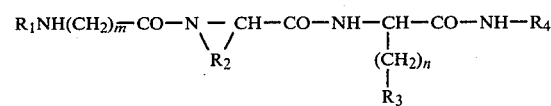

and the biologically acceptable acid addition salts thereof, wherein $R_1$ represents hydrogen or lower alkyl having 1 to 4 carbon atoms; $R_2$ represents an alkylene having 2 to 4 carbon atoms; $R_3$ represents amino or guanidino; $R_4$ represents nitrophenyl, methylnitrophenyl, dinitropheyl, naphthyl, or nitronaphtyl; m is 2 or 3; and n is 3 or 4. The compounds of the present invention are analytical reagents useful for measuring proteolytic enzymes such as thrombin and trypsin. The enzymatic hydrolysis of the invention compounds provides a chromogenic amine by which the proteolytic enzyme concentration can be determined spectrophotometrically.

5 Claims, No Drawings

CHROMOGENIC SUBSTRATES

BACKGROUND OF THE INVENTION

The present invention relates to reagents useful in the quantitative determination of proteolytic enzymes. More particularly the present invention relates to peptide derivatives that are substrates for enzymes of the class E.C.3.4.4. These enzymes cleave amide linkages in peptide chains on the carboxyl side of arginine and lysine residues.

Classical substrates for trypsin, thrombin, and related enzymes have involved amides such as $N^\alpha$-benzoyl-DL-arginyl-p-nitroanilide, L-lysyl-p-nitroanilide, $N^\alpha$-benzoyl-DL-arginyl-2-napthylamide and other di, tri, and higher order arginine and lysine peptides with chromogenic amide leaving groups [B. F. Erlanger, et al., Arch. Biochem. Biophys. 95 (1961) 271; A. Riedel and E. Wunsch, Z. Physiol. Chem. 316 (1961) 1959; R. E. Plapinger, et al., J. Org. Chem. 30 (1965) 1781; L. Svendsen, et al.]. The advantage of extending the amino terminal end of either arginyl or lysyl-p-nitroanilide substrates results in improved behavior [L. Svendsen et al., Thrombosis Res. 1 (1972) 267-78, U.S. Pat. No. 3,884,896].

In particularly U.S. Pat. No. 4,070,245 describes compounds of the general structure:

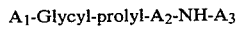

$A_1$-Glycyl-prolyl-$A_2$-NH-$A_3$ wherein $A_1$ represents hydrogen or a blocking acyl or sulfonyl group, $A_2$ represents arginyl or lysyl, and $A_3$ represents an aromatic hydrocarbon group which may carry substituents. More particularly the above Patent discloses the structure:

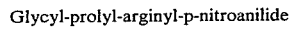

Glycyl-prolyl-arginyl-p-nitroanilide (abbreviated: Gly-pro-arg-pNA)

The above prior art compound is a tripeptide with a N-terminal glycyl and has a turnover rate for the determination of thrombin, which is higher than the turnover rates of the present invention compounds.

This high turnover rate for Gly-pro-arg-pNA results in the compound not being suitable for the determination of thrombin in an automated system performing a plurality of assays over an extended period of time.

U.S. patent application Ser. No. 970,767, filed 12/18/78, describes a homologous compound such as sarcosyl-prolyl-arginyl-p-nitroanilide.

The present invention compounds illustrated typically by the following structures:

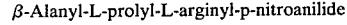

β-Alanyl-L-prolyl-L-arginyl-p-nitroanilide (abbreviated: β-Ala-pro-arg-pNA)

and

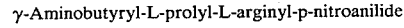

γ-Aminobutyryl-L-prolyl-L-arginyl-p-nitroanilide (abbreviated: Abu-pro-arg-pNA)

are tripeptides preferably with N-terminal β-alanyl or γ-aminobutyryl or derivatives thereof. The invention compounds have unexpectedly suitable turnover rates as substrates for the determination of thrombin and can be used for performance of a plurality of individual assays over an extended period of time, particularly in an automated system.

A number of automated systems have been devised for analyzing the concentration of a particular substance such as thrombin in a chemical specimen such as blood. For example, U.S. Pat. No. 3,748,044 describes a multiple assay system.

In this system assays for thrombin are performed over periods of ten minutes or more. The present invention substrates show linearity of enzyme reaction during the entire time period and permit suitable monitoring and evaluation of all the assays. Prior art substrates that have high turnover rates and do not show such linearity pose a problem in being too highly reactive with thrombin. As is well known in the chemical arts, it is essential for obtaining reliable data that enzymatic assays be performed and evaluated within a period when the rate of the reaction is linear with time [Biochemical Calculations, I. H. Segel, 2nd ed: J. Wiley and Sons Pub. (1976)].

The problem encountered in the use of substrates with high turnover rates may be resolved in part by using very high concentrations of the substrates or very low levels of plasma in the reaction. These are not practical resolutions for the problem in that the use of high substrate concentrations would be very costly, solubility of such substrates in aqueous medium and possible substrate inhibition would present added difficulties, and low levels of plasma would lead to incomplete activation of the factors involved in thrombin generation. The more acceptable resolution for the problem is the employment of substrates with lower turnover rates. The present invention compounds unexpectedly satisfy this need for substrates with lower turnover rates.

BRIEF DESCRIPTION OF THE INVENTION

The present invention comprises compounds of the formula

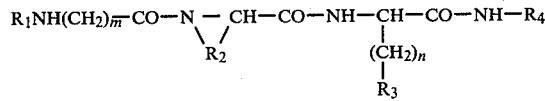

$$R_1NH(CH_2)_m-CO-N-CH-CO-NH-CH-CO-NH-R_4$$
$$\underset{R_2}{\diagdown\diagup} \qquad \underset{\underset{R_3}{|}}{(CH_2)_n}$$

and the biologically acceptable acid addition salts thereof, wherein $R_1$ represents hydrogen or lower alkyl having 1 to 4 carbon atoms; $R_2$ represents an alkylene having 2 to 4 carbon atoms; $R_3$ represents amino or guanidino; $R_4$ represents nitrophenyl, methylnitrophenyl, dinitrophenyl, naphthyl, or nitronaphthyl, m is 2 or 3; and n is 3 or 4. The compounds of the present invention are analytical reagents useful of measuring proteolytic enzymes such as thrombin and trypsin. The enzymatic hydrolysis of the invention compounds provides a chromogenic amine by which the proteolytic enzyme concentration can be determined spectrophotometrically.

DETAILED DESCRIPTION OF THE INVENTION

The present invention encompasses compounds represented by the formula

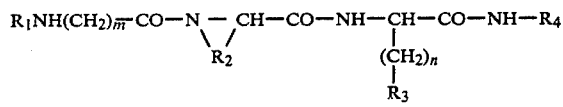
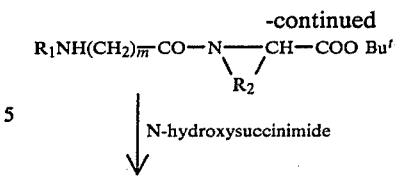

and the biologically acceptable acid addition salts thereof. $R_1$ represents hydrogen or lower alkyl having 1 to 4 carbon atoms such as methyl, ethyl, propyl, isopropyl, butyl, and t-butyl. The m is 2 or 3. $R_2$ represents an alkylene having 2 to 4 carbon atoms belonging to an amino acid residue selected from the group consisting of L-proline (where $R_2$ is propylene), L-pipecolic acid (where $R_2$ is butylene, and L-azetidine carboxylic acid (where $R_2$ is ethylene). $R_3$ represents the amino or guanidino group belonging to an amino acid residue selected from the group consisting of L-arginine or L-ornithine (where n equals 3) or L-lysine or L-homo arginine (where n equals 4). $R_4$ is selected from the group consisting of nitrophenyl, methylnitrophenyl, dinitrophenyl, naphthyl and nitronaphthyl. $R_4$ is preferably nitrophenyl but other art recognized chromogenic substitutes for nitrophenyl may be used [Plapinger, Nachlas, Seligman and Seligman, *J. Organic Chemistry*, 30, (1965) 1781, and U.S. Pat. No. 3,884,896].

Preferred compounds are represented by the formula

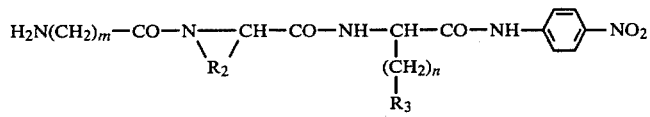

and the biologically acceptable acid addition salts thereof, wherein $R_2$, $R_3$, m and n are as previously defined.

The most preferred compounds are represented by the formula

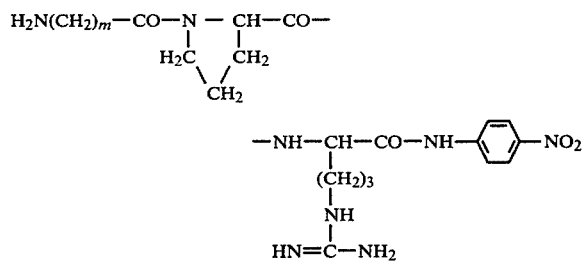

and the biologically acceptable acid addition salts thereof, wherein m is as previously defined.

Compounds of the present invention are prepared by the following scheme:

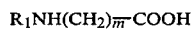

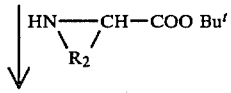

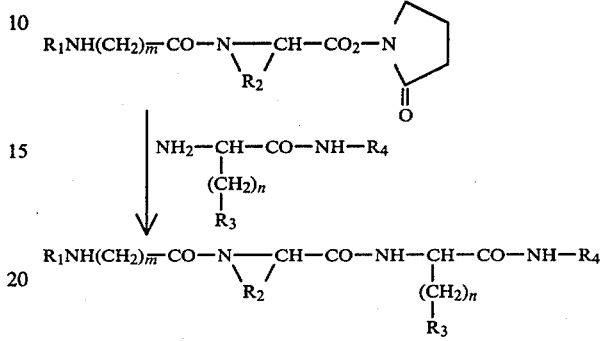

wherein $R_1$, $R_2$, $R_3$, $R_4$, m and n are as previously defined. $Bu^t$ represents tertiary butyl.

Typically, carbobenzoxy-β-alanine is reacted by the mixed anhydride method with L-prolyl t-butyl ester, providing, after treatment with trifluoroacetic acid, carbobenzoxy-β-alanyl-L-proline. This latter product is treated with N-hydroxysuccinimide and dicyclohexylcarboiimide to provide the carbobenzoxy-β-alanyl-L-prolyl succinimidyl ester. The ester is then reacted with the hydrobromide salt of L-arginyl (methoxybenzenesulfonyl)-p-nitroanilide to provide carbobenzoxy-β-alanyl-L-prolyl-L-arginyl (methoxybenzenesulfonyl)-p-nitroanilide whose blocking groups, the carbobenzoxy and methoxybenzenesulfonyl moieties, are removed by a hydrofluoric acid treatment.

In this manner the following representative compounds of the present invention are prepared:

β-alanyl-L-prolyl-L-arginyl-p-nitroanilide,
β-alanyl-L-pipecolyl-L-arginyl-p-nitroanilide,
β-alanyl-L-azetidine carbonyl-L-arginyl-p-nitroanilide,
β-alanyl-L-prolyl-L-lysyl-p-nitroanilide,
β-alanyl-L-pipecolyl-L-lysyl-p-nitroanilide,
β-alanyl-L-prolyl-L-ornithyl-p-nitroanilide,
β-alanyl-L-prolyl-L-ornithyl-p-nitroanilide,
β-alanyl-L-pipecolyl-L-ornithyl-p-nitroanilide,
β-alanyl-L-azetidine carbonyl-L-ornithyl-p-nitroanilide,
γ-aminobutyryl-L-prolyl-L-arginyl-p-nitroanilide,
γ-aminobutyryl-L-pipecolyl-L-arginyl-p-nitroanilide,
γ-aminobutyryl-L-azetidine carbonyl-L-arginyl-p-nitroanilide,
γ-aminobutyryl-L-prolyl-L-lysyl-p-nitroanilide,
γ-aminobutyryl-L-pipecolyl-L-lysyl-p-nitroanilide,
γ-aminobutyryl-L-azetidine carbonyl-L-lysyl-p-nitroanilide,
γ-aminobutyryl-L-propyl-L-ornithyl-p-nitroanilide,
γ-aminobutyryl-L-pipecolyl-L-ornithyl-p-nitroanilide, γ-aminobutyryl-L-azetidinecarbonyl-L-ornithyl-p-nitroanilide, and the biologically acceptable acid addition salts thereof.

The acid addition salts within the scope of the present invention compounds are of the biologically acceptable acid salts selected from mineral acids such as hydrochloric, hydrobromic, hydrosulfuric, and hydrophosphoric or form organic acids such as formic, acetic, oxalic, tartaric, methanesulfonic and benzenesulfonic. Those skilled in the art will recognize the equivalence of other organic and mineral acids.

Another procedure for preparing the present invention compounds involves the coupling of L-prolyl-N$^\omega$-nitro-L-arginyl-p-nitroanilide to a carbobenzoxy-β-alanine N-hydroxy-5-norbornene-2,3,-dicarboximide active ester. The product of this coupling is chromatographed on silica gel and the resulting fractions provide carbobenzoxy-β-alanyl-L-prolyl-N$^\omega$-nitro-L-arginyl-p-nitroanilide which is converted to β-alanyl-L-prolyl-L-arginyl-p-nitroanilide.2HCl by removal of the carbobenzoxy and nitro protecting groups with hydrogen fluoride.

In a typical procedure the enzyme and the substrate are mixed in a buffer solution and the reaction is followed spectrophotometrically. The concentration of substrate is varied, while the enzyme concentration is kept constant. As is well known in the art, a plot of the optical density as a function of time gives a curve from which the rate of reaction can be determined. Correspondingly, a Lineweaver-Burk plot therefrom permits determination of $K_m$ and $K_{cat}$. The turnover rate is represented by $K_{cat}/K_m$.

Table I presents Michaelis-Menten kinetic data and illustrates the usefulness of β-alanyl-L-prolyl-L-arginyl-p-nitroanilide (Ala-pro-arg-pNA) and γ-aminobutyryl-L-prolyl-L-arginyl-p-nitroanilide (Abu-pro-arg-pNA) for determining thrombin and other proteolytic enzymes. The table also presents kinetic data on a prior art compound, Glycylprolyl-arginyl-p-nitroanilide (Gly-pro-arg-pNA). The kinetic data was obtained from reactions run in 0.1 M TRIS-HCl and 0.15 M NaCl buffer at pH 7.4. the reaction mixture contained the enzymes thrombin at $1.5 \times 10^{-8}$ M, kallikrein at $1 \times 10^{-8}$ M, plasmin at $6 \times 10^{-8}$ M, or trypsin at $1 \times 10^{-8}$ M and varying concentrations of the substrates Gly-pro-arg-pNA, β-Ala-pro-arg-pNA, or Abu-pro-arg-pNA in buffer solution. The reaction was analyzed on a Gilford 250 spectrophotometer at 405 nm and 37° centigrade. The rate constants were calculated from the initial rate of reaction against increasing substrate concentrations and constant enzyme concentration under similar conditions.

Clinically, the chromogenic substrates are used to measure antithrombin III. Antithrombin III (AT-III) is the major component of the anticoagulation system. It inhibits a variety of serine proteases by forming a 1:1 complex via serine, the active center of such enzymes. The presence of heparin increases the rate of reactin of AT-III with such proteases approximately 100-fold, making AT-III the only plasma component involved in this rapid inhibition reaction.

The chemistry of the AT-III is described in the following equations:

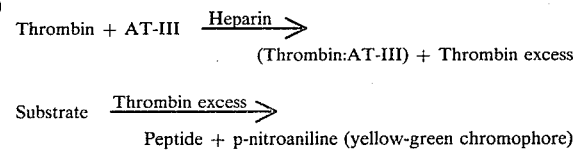

$$\text{Thrombin} + \text{AT-III} \xrightarrow{\text{Heparin}} (\text{Thrombin:AT-III}) + \text{Thrombin excess}$$

$$\text{Substrate} \xrightarrow{\text{Thrombin excess}} \text{Peptide} + \text{p-nitroaniline (yellow-green chromophore)}$$

Since the presence of heparin potentiates the activity of AT-III, it is possible to delineate the inhibition due to AT-III from that of other plasma proteins which can also inhibit thrombin. Thus, one measures total AT-III activity as an entity distinct from the "progressive antithrombin activity" which is measured in the absence of heparin. As a result, one can clearly identify a defect in the anticoagulation system as one associated with AT-III rather than other protein inhibiting mechanisms.

This test relies on the fact that human AT-III in a specimen inhibits human α-thrombin in a 1:1 molar ratio. Excess thrombin is free to hydrolyse a colorless chromogenic substrate is cleaved, it releases, for example, in the absorbance spectrum shown by the development of a yellow-green color. This cleavage of the substrate is analogous to the cleavage of the arginyl-glycine bond in fibrinogen which results in the formation of fibrin. By monitoring the color development of the reaction mixture, one can follow the course of the turnover of substrate by thrombin. Since the amount of AT-III and the amount of color produced are inversely proportional, the level of AT-III can readily be determined.

The following examples illustrate the present invention and are not intended to limit the invention in scope or spirit.

EXAMPLE I

N$^\omega$-methoxybenzenesulfonyl-L-arginyl-p-nitroanilide.HBr 23.0 g. of N$^\alpha$-carbobenzoxy-N$^\omega$-(4-methoxybenzenesulfonyl)-L-arginine is dissolved in 100 ml. of hexamethylphosphoramide. To the resulting solution is added 6.7 ml. of triethylamine and 15.8 g. of p-nitrophenyl isocyanate. The solution is stirred at room temperature overnight and then poured into 1300 ml. of 5% sodium bicarbonate. The resulting precipitate is col-

TABLE I

| | THROMBIN | | | H. KALLIKREIN | | | H. PLASMIN | | | TRYPSIN | | |
|---|---|---|---|---|---|---|---|---|---|---|---|---|
| | | | Turnover Rate | | | Turnover Rate | | | Turnover Rate | | | Turnover Rate |
| SUBSTRATE | Km X10$^{-4}$ M | Kcat Sec$^{-1}$ | Kcat/Km M$^{-1}$ Sec$^{-1}$ X10$^4$ | Km X10$^{-4}$ M | Kcat Sec$^{-1}$ | Kcat/Km M$^{-1}$ Sec$^{-1}$ X10$^4$ | Km X10$^{-4}$ M | Kcat Sec$^{-1}$ | Kcat/Km M$^{-1}$ Sec$^{-1}$ X10$^4$ | Km X10$^{-4}$ M | Kcat Sec$^{-1}$ | Kcat Km M$^{-1}$ Sec$^{-1}$ X10$^4$ |
| (1) Gly-pro-arg-pNA | 2.8 | 43 | 15.0 | 12.4 | 31.0 | 2.5 | 12.5 | 2.3 | 0.18 | 4.1 | 33.0 | 8.0 |
| (2) β-Ala-pro-arg-pNA | 14.0 | 26 | 1.85 | 7.6 | 8.0 | 1.05 | 14 | 1.05 | 0.075 | 2.5 | 7.5 | 3.0 |
| (3) Abu-pro-arg-pNA | 9.1 | 13.3 | 1.4 | 20.0 | 12.6 | 0.63 | 16 | 1.05 | .065 | 3.8 | 11.5 | 3.0 | lected by a filtration funnel and washed separately with (2×400 ml.) 5% sodium bicarbonate, (1×300 ml.) water, (3×300 ml.) 1 N hydrochloric acid and then (2×200 ml.) water. The precipitate is dried in the filtration funnel by vacuum suction and then extracted with (3×300 ml.) boiling methanol. The methanol extracts are combined and the methanol is evaporated in vacuo at 35° C. The semi-solid residue is purified further by a silica gel column using chloroform:acetic acid:methanol (94:5:1) as eluent. This provides $N^\alpha$-carbobenzoxy-$N^\omega$-(4-methoxybenzenesulfonyl)-L-arginyl-p-nitroanilide.

6.0 g. of this material is dissolved in 30% hydrobromic acid in acetic acid. The resulting reaction mixture is kept at room temperature for 45 minutes and then poured into 400 ml. of dry ether. The precipitated salt is filtered and washed with (2×100 ml.) of dry ether to provide $N^\omega$-methoxybenzenesulfonyl-L-arginyl-p-nitroanilide hydrobromide.

EXAMPLE II

Carbobenzoxy-β-alanyl-L-prolyl-$N^\omega$-nitro-L-arginyl-p-nitroanilide 2.1 g. of L-prolyl-$N^\omega$-nitro-L-arginyl-p-nitroanilide trifluoroacetate* is dissolved in a solution containing 10 ml. dimethylformamide 0.95 ml. triethylamine. 1.5 g. of carbobenzoxy-β-alanine N-hydroxy-5-norbornene-2,3-dicarboximide ester [prepared as described by M. Fujino, et. al., Chem. Pharm. Bull. 22 (8), 1957–1863 (1974)] is added to the solution which is then stirred overnight. The solvent is evaporated at 30°–35° C. in vacuo, and the residue is partitioned between water (50 ml.) and ethyl acetate (300 ml.) The ethyl acetate is evaporated at 30°–35° C. in vacuo, and the residue is dissolved in 3 to 4 ml. of methylene chloride and chromatographed on a silica gel column eluting with 2–6% methanol in methylene chloride. Fractions from the column yield carbobenzoxy-β-alanyl-L-prolyl-$N^\omega$-nitro-L-arginyl-p-nitroanilide.

*L-prolyl-$N^\omega$-nitro-L-arginyl-p-nitroanilide trifluoracetate is commercially available from U.S. Biochemicals Corporation.

EXAMPLE III

Carbobenzoxy-β-alanyl-L-proline t-butyl ester 4.46 g. of carbobenzoxy-β-alanine is dissolved in 20 ml. of tetrahydrofuran and the resulting solution cooled to −10° C. With constant stirring of the solution, 2.4 ml. of N-methylmorpholine followed by 2.6 ml. of isobutylchloroformate are added and the resulting reaction mixture is stirred thereafter for approximately 5 minutes at −10° C. 4.16 g. of L-proline t-butyl ester hydrochloride in 20 ml. of dimethylformamide and 2.8 ml. of triethylamine is added to the reaction mixture which is thereafter stirred overnight, while slowly warming to room temperature. The solvent of the reaction mixture is evaporated in vacuo at 30°–35°. The residue is dissolved in 800 ml. of ethyl acetate which is washed with (2×150 ml.) a 10% citric acid solution, with (1×150 ml.) water, with (2×150 ml.) saturated solution of sodium bicarbonate and then with (2×100 ml.) water. The organic layer is dried with anhydrous magnesium sulfate and the solvent evaporated to yield carbobenzoxy-β-alanyl-L-proline t-butyl ester.

EXAMPLE IV

Carbobenzoxy-β-alanyl-L-prolyl-$N^\omega$-methoxybenzenesulfonyl-L-arginyl-p-nitroanilide 1.0 g. of carbobenzoxy-β-alanyl-L-proline t-butyl ester is dissolved in a solution of 5 ml. of methylene chloride and 5 ml. of trifluoroacetic acid. The resulting reaction mixture is allowed to react for approximately 30 minutes at room temperature. The solvent of the reaction mixture is then evaporated in vacuo at room temperature. The residue is washed with (2×50 ml.) benzene which is removed by evaporation in vacuo at room temperature. The residue is dried in vacuo for approximately 5 hours. The residue is dissolved in 10 ml. of tetrahydrofuran and thereafter, 5 ml. of dimethylformamide and 0.5 g. of N-hydroxysuccinimide are added. The solution is cooled to 4° centigrade and 0.52 g. of dicyclohexylcarboiimide is added with stirring that continues for one hour thereafter. To this solution is added sequentially 1.3 g. of $N^\omega$-methoxybenzenesulfonyl-L-arginyl-p-nitroanilide hydrobromide dissolved in 10 ml. of dimethylformamide and then 1.0 ml. of triethylamine. The resulting reaction mixture is stirred at room temperature for approximately 48 hours and the solvent then evaporated at 30°–35° C. in vacuo. The residue is dissolved in 400 ml. of ethyl acetate which is then washed with (2×75 ml.) of 1 N HCl solution, with (1×75 ml.) water, with (2×75 ml.) saturated sodium bicarbonate solution, and again with (1×75 ml.) water. The ethyl acetate layer is then dried with anhydrous magnesium sulfate and evaporated in vacuo at room temperature. The residue is dissolved in ethyl acetate and hexane is added, forming a percipitate which is carbobenzoxy-β-alanyl-L-prolyl-$N^\omega$-methoxybenzenesulfonyl-L-arginyl-p-nitroanilide.

EXAMPLE V

β-alanyl-L-prolyl-L-arginyl-p-nitroanilide.dihydrochloride 450 mg. of carbobenzoxy-β-alanyl-L-prolyl-$N^\omega$-methoxybenzenesulfonyl-L-arginyl-p-nitroanilide is reacted with 15 ml. of liquid hydrofluoride at 0° centigrade for one hour in a Sakakibara Hydrogen Fluoride Reaction Apparatus as described in U.S. Pat. No. 4,070,245. The hydrofluoride is evaporated and the residue mixture is partitioned between 100 ml. of anhydrous ether and 30 ml. of 1 N hydrochloric acid. The aqueous layer is separated and lyophilized. The lyophilized product is dissolved in 1–2 ml. of 30% acetic acid and column chromatographed over sephadex G-25 with an eluting solvent of 30% acetic acid. Appropriate fractions from the column are combined and 1 ml. of 1 N HCl is added. These combined fractions are lyophilized and yield β-alanyl-L-prolyl-L-arginyl-p-nitroanilide dihydrochloride.

EXAMPLE VI

β-alanyl-L-prolyl-L-arginyl-p-nitroanilide dihydrochloride

Following the procedure in Example V replacing carbobenzoxy-β-alanyl-L-prolyl-$N^\omega$-methoxybenzenesulfonyl-L-arginyl-p-nitroanilide with carbobenzoxy-β-alanyl-L-prolyl-$N^\omega$-nitro-L-arginyl-p-nitroanilide yields β-alanyl-L-prolyl-L-arginyl-p-nitroanilide dihydrochloride.

EXAMPLE VII

N-carbobenzoxy-γ-aminobutyric acid

To a solution of 100 ml. of water and 120 ml. of tetrahydrofuran is added sequentially 12.4 g. of γ-aminobutyric acid, 10.4 g. of sodium bicarbonate, and 30 g. of N-benzyloxycarbonyloxysuccinimide. The reaction mixture is stirred for approximately 3.5 hours at room temperature and then the tetrahydrofuran is evaporated in vacuo. The residue is diluted with 200 ml. of water and extracted with (2×300 ml.) anhydrous ether. The aqueous layer is then acidified to pH 1-2 with 1 N hydrochloric acid and extracted with (3×400 ml.) methylene chloride. The methylene chloride extracts are collected and combined and then washed with (3×200 ml.) brine solution, dried with anhydrous magnesium sulfate and the solvent evaporated in vacuo at room temperature. The residue provides N-carbobenzoxy-γ-aminobutyric acid.

EXAMPLE VIII

N-Carbobenzoxy-γ-aminobutyryl-L-prolyl-N$^\omega$-nitro-L-arginyl-p-nitroanilide 474 mg. of N-carbobenzoxy-γ-aminobutyric acid and 345 mg. of N-hydroxy succinimide are dissolved in 6 ml. of dimethylformamide. The resulting solution is cooled in ice water bath to 0° C. and 412 mg. of dicyclohexylcarboiimide is added with stirring of the solution. The resulting reaction mixture is stirred thereafter for approximately one hour. The dicyclohexylcarbodiimide is then removed by filtration. The filtrate is then added dropwise to a solution containing 503 mg. of L-prolyl-N$^\omega$-nitro-L-arginyl-p-nitroanilide trifluoracetate dissolved in 5 ml. of dimethylformamide and 0.5 ml. of triethylamine. The resulting reaction mixture is then stirred at room temperature overnight. The solvent of the reaction is then evaporated at 30°-35° C. in vacuo. The residue is then washed with (2×5 ml.) water. The residue is thereafter dissolved in 2 to 3 ml. of chloroform and chromatographed over a (2.2×30 cm.) silica gel column, eluting with 1-4% methanol in chloroform. Appropriate fractions from the column yield N-carbobenzoxy-γ-aminobutyryl-L-prolyl-N$^\omega$-nitro-L-arginyl-p-nitroanilide.

EXAMPLE IX

γ-aminobutyryl-L-prolyl-L-arginyl-p-nitroanilide dihydrochloride 118 mg. of N-carbobenzoxy-γ-aminobutyryl-L-prolyl-N$^\omega$-nitro-L-arginyl-p-nitroanilide is reacted with 10 ml. of liquid hydrofluoride at 0° centigrade for one hour in a Sakakibara Hydrogen Fluoride Reaction Apparatus as described in U.S. Pat. No. 4,070,245. The hydrogen fluoride is evaporated and the residual mixture is partitioned between 100 ml. of anhydrous ether and 30 ml. of 1 N hydrochloric acid. The aqueous layer is separated and lyophilized. The lyophilized product is dissolved in 2-3 ml. of 30% acetic acid and column chromatographed over Sephadex G-25 eluting with a solvent of 30% acetic acid. Appropriate fractions from the column are combined and 1 ml. of 1 N HCl is added. The combined fractions are lyophilized and yield γ-aminobutyryl-L-prolyl-L-arginyl-p-nitroanilide 2-hydrochloride.

EXAMPLE X

N-Carbobenzoxy-4-ethylaminobutyric acid

Following the procedure in Example VII replacing γ-aminobutyric acid with 4-ethyl aminobutyric acid [prepared as described by W. Reppe, Ann. 596,201 (1955)] provides N-carbobenzoxy-4-ethylaminobutyric acid.

EXAMPLE XI

N-Carbobenzoxy-4-ethylaminobutyryl-L-prolyl-N$^\omega$-nitro-L-arginyl-p-nitroanilide Following the procedure in Example VIII replacing N-carbobenzoxy-γ-aminobutyric acid with N-carbobenzoxy-4-ethylaminobutyric acid yields, after chromatography, N-carbobenzoxy-4-ethylaminobutyryl-L-prolyl-N$^\omega$-nitro-L-arginyl-p-nitroanilide.

EXAMPLE XII 4-ethylaminobutyryl-L-prolyl-L-arginyl-p-nitroanilide dihydrochloride Following the procedure in Example IX replacing N-carbobenzoxy-γ-amino-butyryl-L-prolyl-N$^\omega$-nitro-L-arginyl-p-nitroanilide with N-carbobenzoxy-4-ethylaminobutyryl-L-prolyl-N$^\omega$-nitro-L-arginyl-p-nitroanilide yields, after chromatography, 4-ethylaminobutyryl-L-prolyl-L-arginyl-p-nitroanilide dihydrochloride.

What is claimed is:

1. A compound of the formula

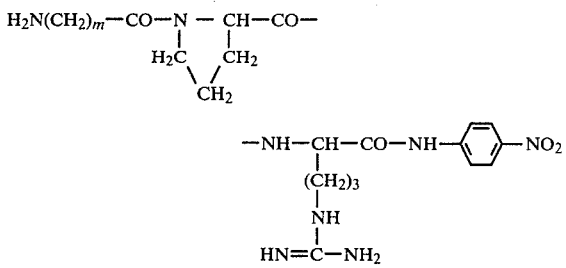

and the biologically acceptable acid addition salts thereof, wherein m is 2 or 3.

2. A compound according to claim 1 which is β-alanyl-L-prolyl-L-arginyl-p-nitroanilide.

3. A compound according to claim 1 which is β-alanyl-L-prolyl-L-arginyl-p-nitroanilide hydrochloride.

4. A compound according to claim 1 which is γ-aminobutyryl-L-prolyl-L-arginyl-p-nitroanilide.

5. A compound according to claim 1 which is γ-aminobutyryl-L-prolyl-L-arginyl-p-nitroanilide hydrochloride.

* * * * *